US006804555B2

(12) United States Patent
Warkentin

(10) Patent No.: US 6,804,555 B2
(45) Date of Patent: Oct. 12, 2004

(54) MULTI-SITE VENTRICULAR PACING SYSTEM MEASURING QRS DURATION

(75) Inventor: Dwight H. Warkentin, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

(21) Appl. No.: 09/896,281

(22) Filed: Jun. 29, 2001

(65) Prior Publication Data

US 2003/0004548 A1 Jan. 2, 2003

(51) Int. Cl.⁷ ............................................... A61N 1/368
(52) U.S. Cl. ........................................ 607/9; 600/516
(58) Field of Search ................................. 600/373, 374, 600/504, 516, 521; 607/4, 5, 9, 11, 14

(56) References Cited

U.S. PATENT DOCUMENTS

| | | |
|---|---|---|
| 3,937,226 A | 2/1976 | Funke |
| 4,088,140 A | 5/1978 | Rockland et al. |
| 4,332,259 A | 6/1982 | McCorkle, Jr. |
| 4,354,497 A | 10/1982 | Kahn |
| 4,428,378 A | 1/1984 | Anderson et al. |
| 4,458,677 A | 7/1984 | McCorkle, Jr. |
| 4,548,203 A | 10/1985 | Tacker, Jr. et al. |
| 4,928,688 A | 5/1990 | Mower |
| 4,972,834 A | 11/1990 | Begemann et al. |
| 5,052,388 A | 10/1991 | Sivula et al. |
| 5,174,289 A | 12/1992 | Cohen |
| 5,267,560 A | 12/1993 | Cohen |
| 5,331,966 A | 7/1994 | Bennett et al. |
| 5,403,356 A | 4/1995 | Hill et al. |
| 5,514,161 A | 5/1996 | Limousin |
| 5,514,163 A | 5/1996 | Markowitz et al. |
| 5,527,347 A | 6/1996 | Shelton et al. |
| 5,674,259 A | 10/1997 | Gray |
| 5,720,768 A | 2/1998 | Verboven-Nelissen |
| 5,749,906 A * | 5/1998 | Kieval et al. .................. 607/9 |
| 5,792,203 A | 8/1998 | Schroeppel |
| 5,797,970 A | 8/1998 | Pouvreau |
| 5,902,324 A * | 5/1999 | Thompson et al. ............ 607/9 |
| 6,070,100 A * | 5/2000 | Bakels et al. .................. 607/9 |
| 6,129,744 A * | 10/2000 | Boute .......................... 607/25 |
| 6,141,586 A | 10/2000 | Mower |

OTHER PUBLICATIONS

Daubert et al., "Permanent Dual Atrium Pacing in Major Intra-atrial Conduction Blocks: A Four Years Experience", *PACE* (vol. 16, Part II, NASPE Abstract 141, p. 885, Apr. 1993).

(List continued on next page.)

*Primary Examiner*—Kennedy Schaetzle
*Assistant Examiner*—Frances P. Oropeza
(74) *Attorney, Agent, or Firm*—Girma Wolde-Michael; Paul H. McDowall

(57) ABSTRACT

Bi-Ventricular or AV synchronous cardiac pacing systems that pace and sense in at least one atrial heart chamber and deliver ventricular pacing pulses to right ventricular (RV) and left ventricular (LV) sites separated by a V—V delay for treatment of heart failure are disclosed that optimize one or more of the AV delay and V—V delay to enhance left ventricular filling and cardiac output as a function of QRS duration.

A system and method for monitoring the QRS duration, processing such signals to provide data from which the onset or progression of heart failure is determined, and adjusting synchronous pacing delay parameters including SAV delay and/or PAV delay and/or V—V delay to enhance cardiac output as a function of QRS duration is provided. The SAV, PAV, and/or the V—V delays can be varied from the prevailing delays as a function of measured QRS duration so as to minimize the width of the QRS complex.

7 Claims, 9 Drawing Sheets

OTHER PUBLICATIONS

Daubert et al., "Permanent Left Ventricular Pacing With Transvenous Leads Inserted Into The Coronary Veins", *PACE* (vol. 21, Part II, pp. 239–245, Jan. 1998).

Cazeau et al., "Four Chamber Pacing in Dilated Cardiomyopathy", *PACE* (vol. 17, Part II, pp. 1974–1979, Nov. 1994).

Daubert et al., "Renewal of Permanent Left Atrial Pacing via the Coronary Sinus", *PACE* (vol. 15, Part II, NASPE Abstract 255, p. 572, Apr. 1992).

Durrer et al., "Total Excitation of the Isolated Human Heart", Circulation, (vol. XLI, pp. 899–912, Jun. 1970).

Lieberman et al., "Relationship Between Electrical and Hemodynamic Parameters Using Bi–Ventricular and Uni–Ventricular Pacing in Heart Failure Patients", JACC (Abstract 1059–69, p. 155A, Feb. 2001).

Cochlain et al., "The Effects of the Interval Between Right and Left Ventricular Activation on Sychronization in Patients with Bi–ventricular Pacemakers", PACE (vol. 23, Part II, NASPE Abstract 94, p. 576, Apr. 2000).

\* cited by examiner

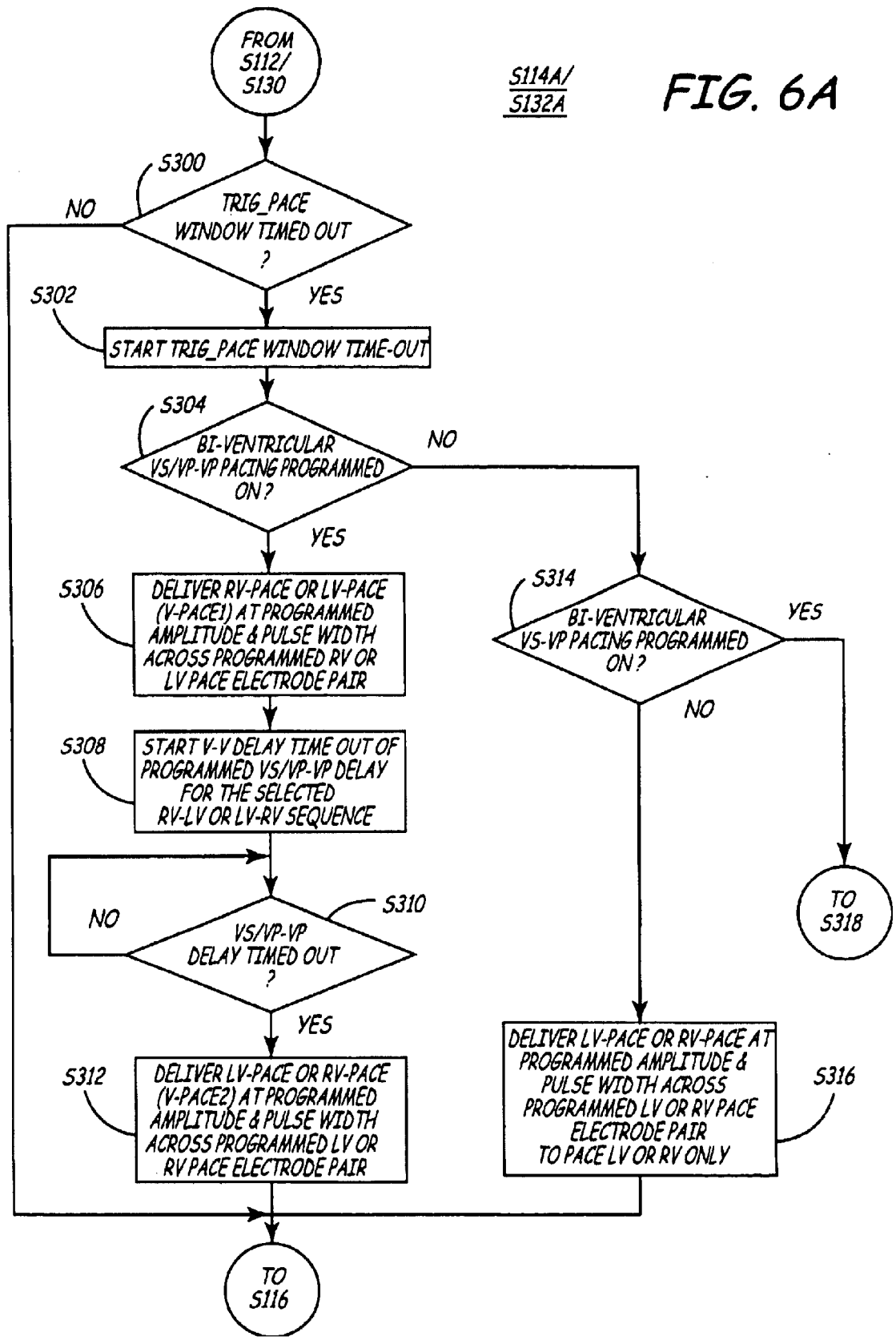

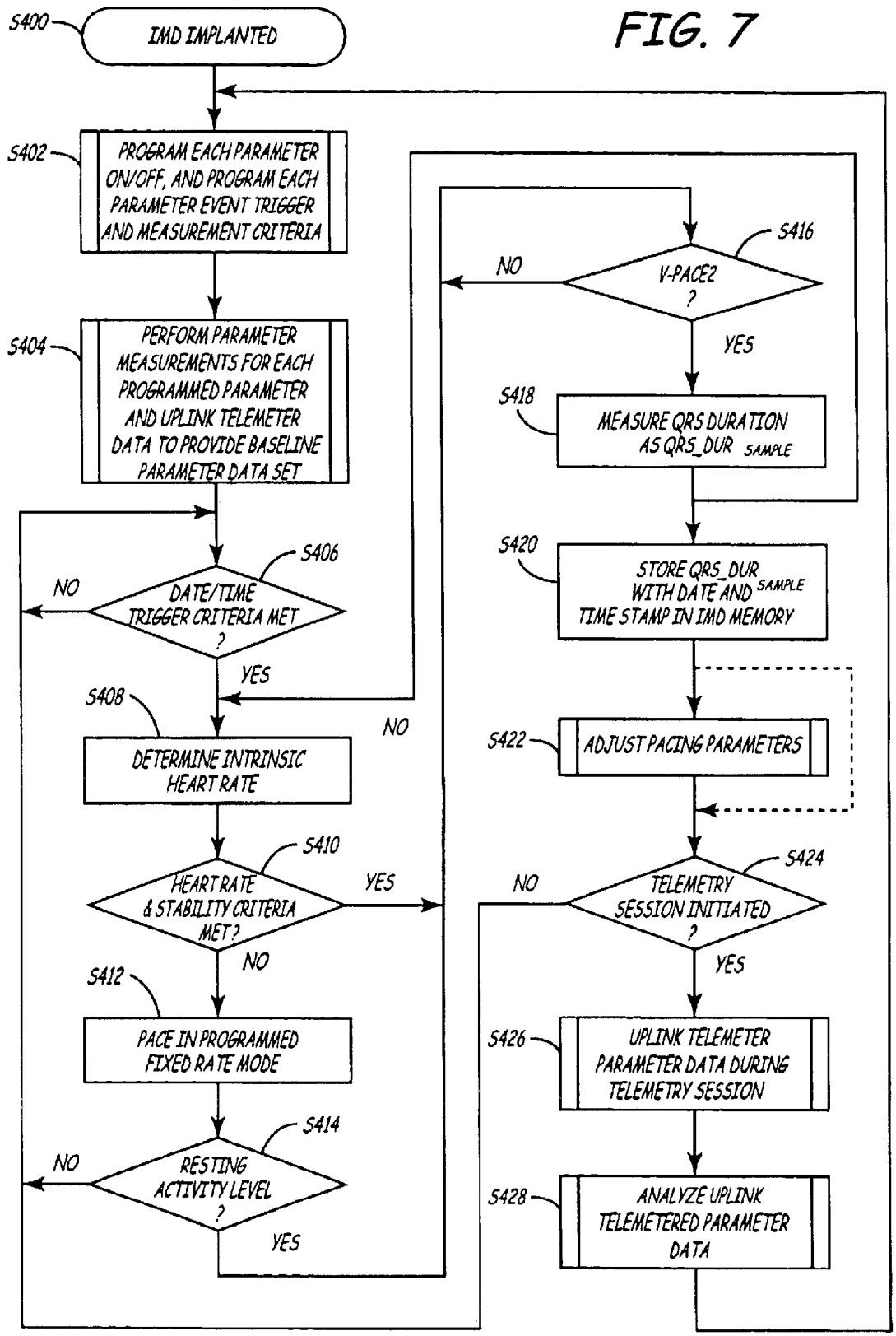

US 6,804,555 B2

MULTI-SITE VENTRICULAR PACING SYSTEM MEASURING QRS DURATION

FIELD OF THE INVENTION

The present invention pertains to multi-site ventricular pacing systems, and particularly Bi-Ventricular and AV synchronous cardiac pacing systems that pace and sense in at least one atrial heart chamber and deliver ventricular pacing pulses to right ventricular (RV) and left ventricular (LV) sites separated by a V—V delay for treatment of heart failure, and particularly to measuring QRS duration as a heart failure parameter and optimizing the AV delay and/or V—V delay to enhance ventricular filling and cardiac output as a function of QRS duration.

BACKGROUND OF THE INVENTION

Congestive heart failure (CHF) is defined generally as the inability of the heart to deliver enough blood, i.e., to supply sufficient cardiac output, to the peripheral tissues to meet metabolic demands. Frequently CBF is manifested by left ventricular dysfunction (LVD), but it can have a variety of sources. For example, CHF patients may have any one of several different conduction defects. The natural electrical activation system through the heart involves sequential events starting with the sino-atrial (SA) node, and continuing through the atrial conduction pathways of Bachmann's bundle and intemodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium to the left atrium. In left bundle branch block (LBBB) and right bundle branch block (RBBB), the activation signals are not conducted in a normal fashion along the right or left bundle branches respectively. Thus, in a patient with bundle branch block, the activation of the ventricle is slowed, and the QRS is seen to widen due to the increased time for the activation to traverse the conduction path. For example, in a patient with LBBB, the delay in the excitation from the RV to the LV can be as high as 120 to 150 ms.

In diseased hearts exhibiting LVD and CHF, cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

More particularly, as described in commonly assigned U.S. Pat. No. 6,129,744, LVD and other forms of heart failure are manifested by reduced ejection fraction from the left ventricle thereby reducing stroke volume and pulmonary edema limiting the patient's ability to exercise. Patients suffering from LVD are also known to have elevated levels of catecholamines at rest because the body is attempting to increase cardiac output that induce a higher resting heart rate. In addition, the QT interval for such a patient is affected by the catecholamine level and thus has a changed pattern during exercise as well. These patients have a decreased QT response, or smaller change in QT, during exercise, such that the QT interval shortening during exercise is smaller than that found normally. Although QT interval is influenced independently by heart rate alone, as well as by exercise and catecholemines, it is not known to what extent each of these factors or both are responsible for the changed QT response to exercise in LVD patients. However, it is known that patients suffering LVD clearly have a different pattern of QT interval shortening during exercise. Moreover, the changed conductive patterns or a heart in heart failure are manifested by other changes in the PQRST waveforms, particularly an abnormally wide or long duration of the ventricular depolarization signal, or QRS.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at least one of the electrode sites. It is believed that atrial and left ventricular cardiac output can be significantly improved when left and right chamber synchrony is restored, particularly in patients suffering from dilated cardiomyopathy, LVD and CHF.

A number of proposals have been advanced for providing pacing therapies to alleviate heart failure conditions and restore synchronous depolarization and contraction of a single heart chamber or right and left, upper and lower, heart chambers as described in detail in the above referenced '744 patent and in commonly assigned U.S. Pat. Nos. 5,403,356, 5,797,970, 5,902,324, and 6,070,100 and in U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514, 161, and 5,584,867.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992).

In the above-referenced '324 patent, an AV synchronous pacing system is disclosed providing three or four heart chamber pacing through pace/sense electrodes located in or adjacent one or both of the right and left atrial heart chambers and in or adjacent to the right and left ventricular heart chambers. During an AV delay and during a V-A escape interval, a non-refractory ventricular sense event detected at either the right or left ventricular pace/sense electrodes starts a conduction delay window (CDW) timer. A ventricular pace pulse is delivered to the other of the left or right ventricular pace/sense electrodes at the time-out of the CDW if a ventricular sense event is not detected at that site while the CDW times out.

The above-referenced '744 patent discloses a rate responsive, bi-ventricular pacemaker having one or more sensors for sensing a parameter indicative of the physiologic need for cardiac output, and for pacing the patient on demand between a lower rate limit (LRL) and an upper rate limit (URL). In a specific embodiment, the pacemaker determines QT interval, and stores data representative of changes in QT interval as a function of paced heart rate and/or the patient's spontaneous lower rate when at rest. Variations in the correlation of QT interval and heart rate, and/or variations in patient lower rate at rest are processed to provide a time trend, or profile, from which a determination is made as to whether or not LVD is indicated. In alternate embodiments, other data derived from cardiac signals is processed and stored, e.g., QRS duration, T-wave amplitude, etc. A change in the variation of T-wave amplitude with respect to exercise, and consequent heart rate, can be easily measured and tracked in a QT rate responsive pacemaker, or any pacemaker adapted to sense and recover the T-waves. Likewise, as noted above, changes in QRS duration (width) and/or morphology may also be detected and tracked for detection of a trend. Trends in this data are periodically evaluated, e.g., on a daily basis, and stored for downloading to an external programmer for deriving an indication of LVD, or onset or progression of LVD or for automatic initiation of a treatment response signals.

In the '744 patent, an algorithm for automatically adjusting the rate responsive parameters, i.e., the correlation function between QT and desired rate is suitably performed on a daily basis. The pacemaker measures a slope of the correlation function at the LRL, and adjusts the QT-rate function between LRL and URL accordingly as disclosed in commonly assigned U.S. Pat. No. 4,972,834. If such changes are stored and analyzed for a trend, progress toward LVD can be indicated. Likewise, if it is found that the patient heart rate is not dropped to the programmed LRL during nighttime, such that the spontaneous lower rate has had an upward progression, this trend can also be used as an indicator of the onset of LVD.

As asserted in the '744 patent, these functions can be performed in an implanted monitor solely dedicated to detection and storage of cardiac data and processing of such data to provide an indication of LVD when interrogated. In a more preferred embodiment, a rate responsive pacemaker system is disclosed that can pace and sense in any combination or all of the four cardiac chambers. The treatment response upon an indication of onset of LVD has a number of embodiments, including changing the rate response function; changing physiologic sensor blending for dual or plural sensor rate responsive pacemakers; initiating three or four chamber pacing to achieve improved left heart response, e.g., synchronous ventricular pacing and/or other multi-chamber sequential pacing; and providing for a measured release of an appropriate drug for treating the LVD. In yet another disclosed embodiment, the pacemaker is implanted with software for carrying out normal dual chamber pacing, but the software can be upgraded by programmer downloading to provide different pacing functions, or to function as a three or four chamber pacemaker, along with utilization of an additional lead or leads for delivering stimulus pulses to the left heart chambers.

In commonly assigned U.S. Pat. No. 5,749,906, a dual chamber pacing system, is disclosed that continually adjusts the AV delay so as to maintain optimal ventricular pacing for therapy of patients having cardiomyopathy. The QRS duration of paced ventricular events is monitored, and analyzed to determine if the paced ventricular event is a fusion beat with an intrinsic ventricular depolarization. If fusion beat frequency criteria established for the patient are met, then the AV delay is shortened incrementally so that the ventricular pace pulse is delivered earlier, and fewer fusion beats occur.

Chronically collected data from patients with progressive LVD or other types of heart failure is needed so that the treating cardiologist can properly and accurately chart the progression, determine the nature of the heart failure, and be able to implement the optimal treatment in a timely fashion. There is also a substantial need in the art for a pacemaker or other implantable medical device (IMD) incorporating three or four channel pacing having the capacity to optimize the AV delay and the V—V pacing delay for pacing the RV and LV to treat the changing patient condition.

SUMMARY OF THE INVENTION

In view of the above need, the present invention provides a system and method for monitoring patient cardiac signals and processing such signals within IMD to provide data from which the onset or progression of heart failure can be determined, particularly the QRS duration as measured during a paced depolarization of the heart, and optimizing synchronous pacing delay parameters to minimize the measured QRS duration.

The present invention is implemented in a wide variety of ways. In the broadest context, the present invention pertains to cardiac pacing systems that pace or sense ventricular events (V-EVENT) at or deliver a first ventricular pace (V-PACE1) pulse to a first ventricular site and deliver a ventricular pace (V-PACE2) pulse to a second ventricular site spaced from the first ventricular site after a V—V delay from the V-EVENT or V-PACE1. A measurement of the cardiac depolarization QRS duration is initiated upon delivery of the V-PACE2. The QRS duration can be retained in IMD memory for retrieval and analysis at a later time or transmitted to a remote external medical device in real time. A series of QRS duration times can be measured and processed to determine maximum, minimum and average QRS duration that are stored in memory.

The QRS duration is preferably measured from a selected pair of sense electrodes located remote from the first and second ventricular sites.

The present invention is preferably implemented in a bi-ventricular pacing system wherein the first ventricular site is one of an RV site or an LV site and the second ventricular site is the other of the RV or LV site, whereby pacing pulses V-PACE1 and V-PACE2 are delivered in the RV-LV sequence or the LV-RV sequence. The V-PACE1 can be delivered either upon the time-out of a pacing escape interval or upon the V-EVENT occurring prior to time-out of the escape interval. The QRS duration can be measured from the V-PACE2 pulse following time-out of the V—V delay timed from a V-EVENT (a VS marker), a V-PACE1 delivered upon a V-EVENT (a VS/VP marker) or a V-PACE1 (a VP marker).

The present invention is also preferably implemented in a three or four chamber pacing system wherein pacing and sensing at one or both of an RA site and an LA site are provided. Bi-ventricular pacing in the LV and RV is provided, wherein V-PACE1 may be delivered to one of the LV site or RV site after time-out of a SAV delay from an atrial event (A-EVENT) sensed at one of the RA or LA sites or a PAV delay an atrial pace pulse delivered to one of the RA or LA sites. V-PACE2 is delivered to the other of the LV site or RV site after time-out of the V—V delay.

Accordingly, this invention provides a system and method for monitoring the QRS duration, processing such signals to provide data from which the onset or progression of heart failure is determined, and adjusting synchronous pacing delay parameters including SAV delay and/or PAV delay and/or V—V delay to enhance cardiac output as a function of QRS duration. The SAV delay and/or the PAV delay and/or the V—V delay can be varied from the prevailing delays as a function of measured QRS duration so as to minimize the width of the QRS complex.

In accordance with one aspect of the present invention, the optimal V—V delay and optionally the optimal PAV delay or SAV delay or the combination of the same that minimizes the measured QRS duration and maximizes mechanical heart performance is determined. In one variation of this aspect of the invention, the SAV delay and/or PAV delay and/or V—V delay providing the minimum QRS duration is derived by successively applying incremented or decremented ones of the SAV delay, PAV delay and/or V—V delay, deriving a $QRS\_DUR_{SAMPLE}$ value at each adjusted delay, comparing the set of N derived $QRS\_DUR_{SAMPLE}$ values to determine the minimum $QRS\_DUR_{SAMPLE}$ value, and setting the SAV delay, PAV delay and/or V—V delay to the SAV delay, PAV delay and/or V—V delay that provides the minimum $QRS_{13} DUR_{SAMPLE}$ value.

Another manner of determining the values of the SAV delay, PAV delay, and/or V—V delay that provide a minimal QRS duration ($QRS_{13} DUR_{MIN}$) following delivery of the V-PACE2 involves measuring the $QRS_{13} DUR_{SAMPLE}$ values after a change in one or more of the V—V delay, SAV delay, and PAV delay are compared with the preceding or prior measured $QRS_{13} DUR_{SAMPLE}$ value to determine if the change has decreased the QRS duration. An additional change in the same direction (increasing or decreasing the parameter duration) is made if the prior change does decrease the QRS duration. But, if the change results in an increase in the measured QRS duration, then the change direction is reversed to repeat the measurement of the QRS duration using the prior parameter value. A rest period of a number of heart cycles or a time period is provided between each change in a V—V delay, SAV delay, and PAV delay parameter value to allow the heart to acclimate to the change.

These methods can be first practiced by the physician in the initial post-implant telemetry session to derive and store in IMD memory the SAV delay, PAV delay and/or V—V delay that affords the shortest QRS duration that is also retained in memory as the QRS DURRF value. The methods are then performed at a programmed time of day preferably when the patient is at rest and the patient's heart rate is low and stable. The derived SAV delay, PAV delay and/or V—V delay that affords the shortest QRS duration are then employed until the next programmed time of day or other event criteria are met.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 6A–6B is a flow chart illustrating the steps of delivering ventricular pace pulses following a ventricular sense event during the time-out of an AV delay or the V-A escape interval in FIG. 4;

FIG. 7 is a flow chart illustrating the steps of periodically determining the QRS duration, storing the QRS duration data, and telemetering the stored data to an external programmer.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, three chamber or four chamber, pacing system operating in demand, atrial tracking, and triggered pacing modes in accordance with FIGS. 4 through 6A–6B for restoring synchrony in depolarizations and contraction of left and right ventricles in synchronization with atrial sensed and paced events for treating bradycardia in those chambers. This embodiment of the invention is programmable to operate as a three or four chamber pacing system having an AV synchronous operating mode for restoring upper and lower heart chamber synchronization and right and left atrial and/or ventricular chamber depolarization synchrony. Of course, the present invention may also be practiced in a simpler, three-chamber pacing system eliminating certain of the features of the preferred embodiment described herein.

It should be appreciated that the present invention may be utilized particularly to treat patients suffering various forms of heart failure with or without bradycardia. The pacing system of the present invention can also be incorporated into an anti-tachyarrhythmia system including specific high rate pacing and cardioversion shock therapies for providing staged therapies to treat a diagnosed tachyarrhythmia.

Figure 1:
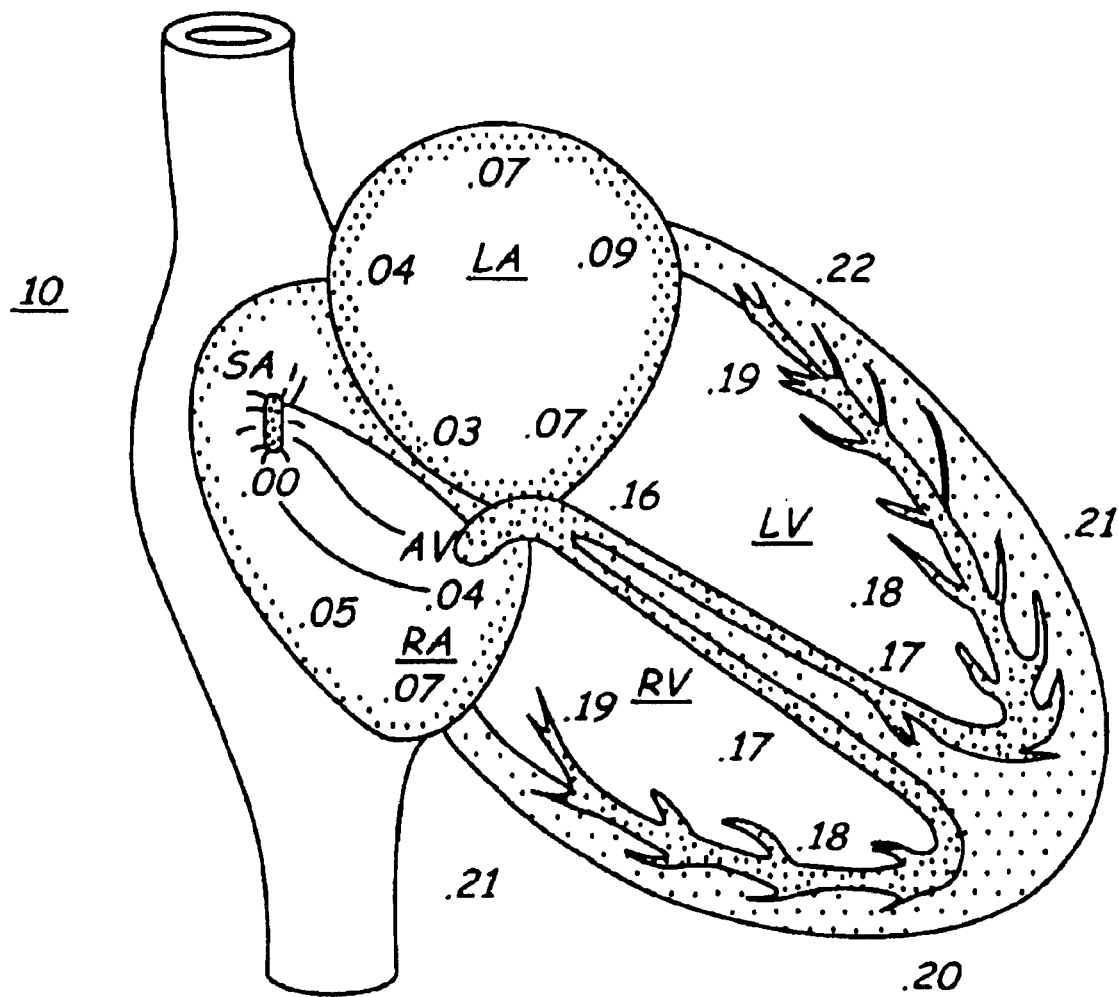
FIG. 1 is an illustration of transmission of the cardiac depolarization waves through the heart in a normal electrical activation sequence.

In FIG. 1, heart 10 includes the upper heart chambers, the RA and LA, and the lower heart chambers, the RV and LV and the coronary sinus (CS) extending from the opening in the RA laterally around the atria to form the great vein (GV) that extends further inferiorly into branches of the GV. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intraventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying repolarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting Intra-Atrial Cardiac Dysfunction (IACD), LBBB, RBBB, and/or IVCD (Intra-Ventricular Cardiac Dysfunction). These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with an aspect of the present invention, a method and apparatus is provided to restore the depolarization sequence of FIG. 1 and the synchrony between the right and left ventricular heart chambers that contributes to adequate cardiac output based upon QRS duration. This restoration is effected through providing optimally timed cardiac pace pulses to the right and left ventricles as necessary and to account for the particular implantation sites of the pace/sense electrodes in relation to each heart chamber while maintaining AV synchrony. The present invention efficiently provides pacing at multiple ventricular pacing sites in a triggered pacing mode in response to a ventricular sense event detected at either ventricular pace/sense electrode site during the AV delay only.

Figure 2:
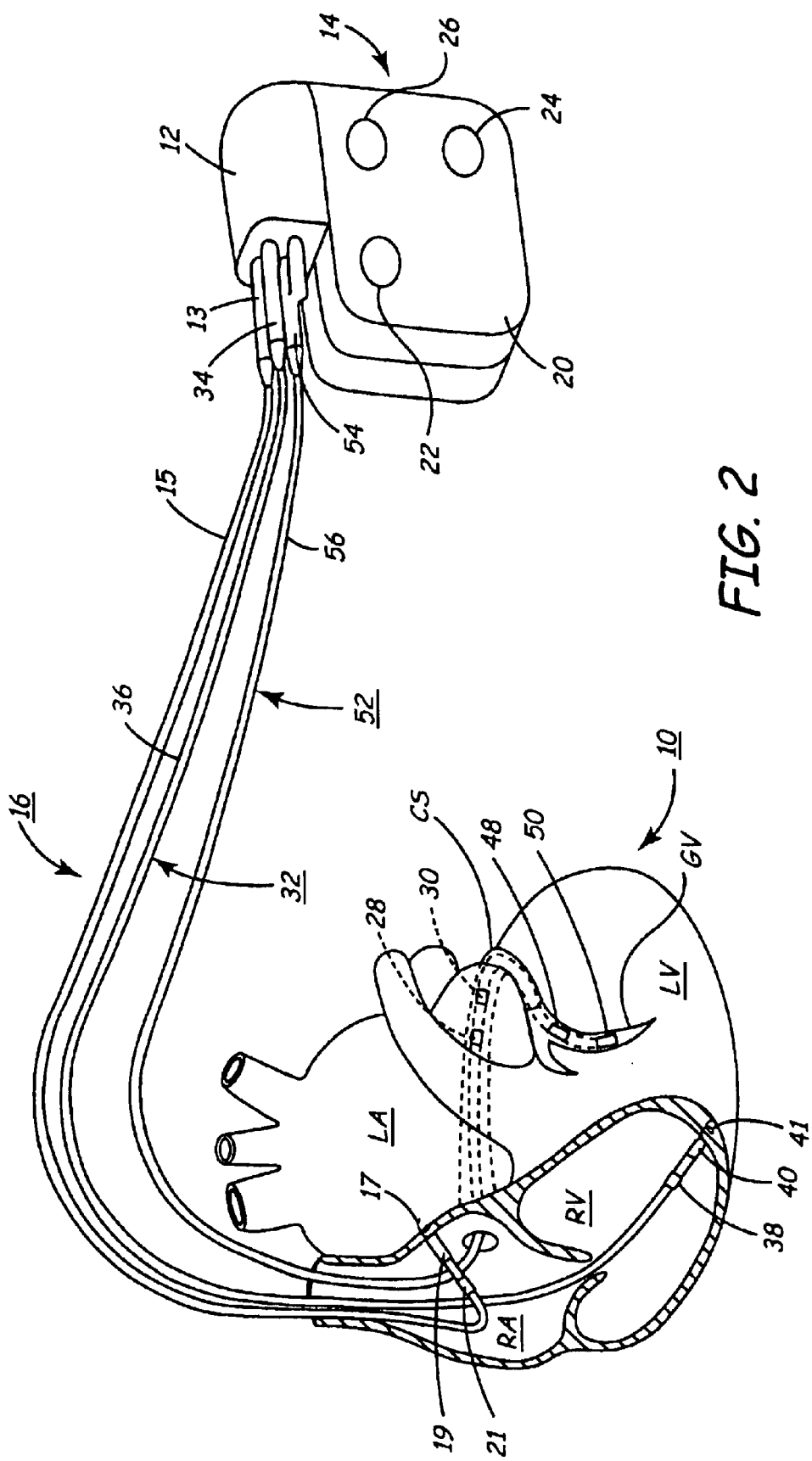
FIG. 2 is a schematic diagram depicting a four channel, bi-atrial and bi-ventricular, pacing system in which the present invention is preferably implemented.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and the LV, respectively, through connections made in the IPG connector block 14. A remote indifferent can electrode may be formed as part of the outer surface of the housing of the IPG 14. In addition, a plurality of electrodes 22, 24 and 26 may be formed in an array on the outer surface of the housing or the connector block 14 in a manner described in commonly assigned U.S. Pat. No. 5,331,966. These electrodes may be selectively employed to measure the QRS ration as described further below.

Any of the housing electrodes may be designated as a remote indifferent an electrode. For discussion purposes, this indifferent can electrode will be referred to hereinafter as "IND_CAN electrode 20". This electrode may be employed in unipolar pacing and sensing combinations with a pace/sense electrode of one or more of the depicted leads 16, 32 and 52. The depicted positions of the pace/sense electrodes in or about the right and left heart chambers are also merely exemplary. Other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG 2 connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial fly lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip fly pace/sense electrode 40 and proximal ring RV pace/sense electrode 38 can be employed with the IND_CAN electrode 20 for unipolar pacing and/or sensing.

In this illustrated embodiment, a bipolar, endocardial CS lead 52 is passed through a vein and the RA chamber of the heart 10, into the CS and then inferiorly in a branching vessel of the great vein GV to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus (CS), and into a coronary vein descending from the coronary sinus, such as the great vein (GV).

In a four chamber or channel embodiment, LV CS lead 52 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
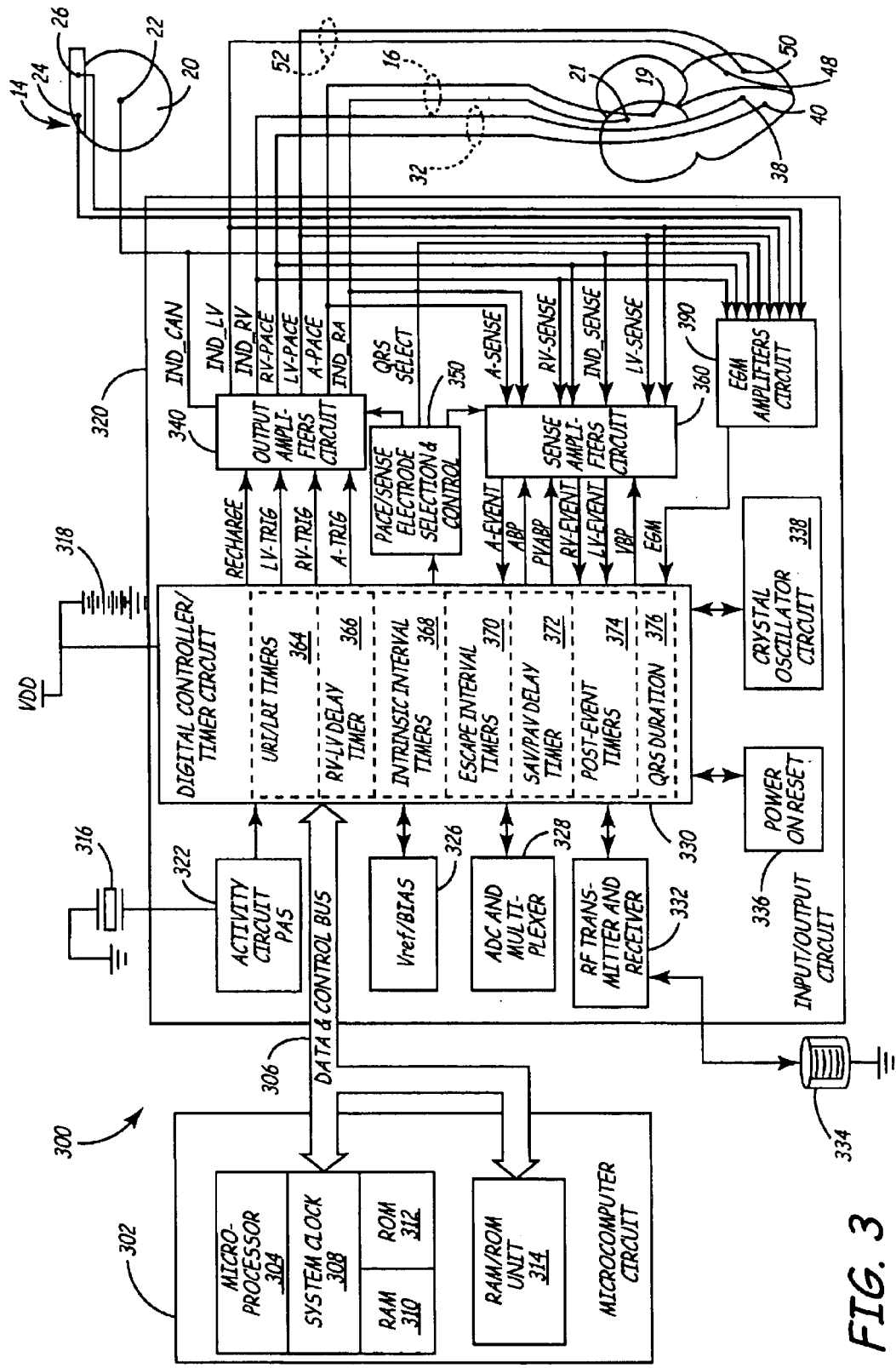
FIG. 3 is a simplified block diagram of one embodiment of IPG circuitry and associated leads employed in the system of FIG. 2 for providing four pacing channels that are selectively programmed in bi-atrial and/or bi-ventricular pacing modes.

In this regard, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 332, the activity sensor circuit 322, the EGM amplifiers circuit 390, and a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via transceiver 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 322 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and transceiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 may be awakened in response to defined interrupt events, which may include A-TRIG, RV-TRIG, and LV-TRIG signals generated by timers in digital timer/controller circuit 330, and/or A-EVENT, RV-EVENT, and LV-EVENT signals generated by sense amplifier circuit 360, among others. The specific values of the intervals and delays timed by digital controller/timer circuit 330 are controlled by the microcomputer circuit 302 by means of data and control bus 306 from programmed-in parameter values and operating modes. In addition, if programmed to operate as a rate responsive pacemaker, a timed interrupt at a predetermined interval such as every two seconds, may be provided in order to allow the microprocessor to analyze the sensor data and update the basic A—A, V-A and/or V—V escape intervals. In addition, in a preferred embodiment of the invention, the microprocessor 304 may also serve to define variable AV delays and the bi-ventricular V—V delays in accordance with the routines illustrated in FIGS. 4–8.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially-available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include an upper rate interval (URI) timer 364, V—V delay timer 366, an intrinsic interval timer 368 for timing elapsed V-EVENT to V-EVENT intervals or V-EVENT to A-EVENT intervals, escape interval timers 370 for timing A—A, V-A, and/or V—V pacing escape intervals, an AV delay interval timer 372 for timing an AV delays from a preceding A-EVENT (SAV delay) or A-TRIG (PAV delay), and a post-event timer 374 for timing post-ventricular time periods. RHC pace trigger and sense events are typically used for starting and resetting these intervals and periods. However, it would be possible to allow the physician to select and program trans-chamber or LHC pace trigger and sense events for these timing purposes.

The post-event timer 374 times the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV delay or PAV delay started by an A-EVENT or an A-TRIG.

It should be noted that the starting of the post-atrial time periods and the AV delays can be commenced substantially simultaneously with the start or end of the A-EVENT or the A-TRIG or, in the latter case, upon the start of end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the start of end of the V-PACE which may follow the V-TRIG.

The microprocessor 304 also optionally calculates AV delays, post-ventricular time periods, and post-atrial time periods that vary with the sensor based escape interval established in response to the RCP(s) and/or with the intrinsic atrial rate. The variable AV delays are usually derived as a fraction of a maximum AV delay set for the pacing LRL (i.e., the longest escape interval). In accordance with one aspect of the present invention, the AV delays can be varied from the prevailing AV delay as a function of measured QRS duration so as to minimize the width of the QRS complex.

The output amplifiers circuit 340 includes switching circuits for coupling selected pace/sense electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace/sense electrode pairs to be coupled with the atrial and ventricular output amplifiers within output amplifiers circuit 340 for accomplishing RA, LA, RV and LV pacing.

The output amplifiers circuit 340 includes switching circuits for coupling selected pace/sense electrode pairs from among the lead conductors and the IND_CAN electrode 22 to the RA pace pulse generator (and LA pace pulse generator if provided), RV pace pulse generator and LV pace pulse generator. Pace/sense electrode pair selection and control circuit 350 selects lead conductors and associated pace/sense electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers in sense amplifiers circuit 360 are uncoupled from the sense electrodes during the blanking periods before, during, and after delivery of a pace pulse to any of the pace/sense electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in an LA-EVENT signal that is communicated to the digital controller/timer circuit 330. Ventricular depolarizations or R-waves in the RV-SENSE signal are sensed by a ventricular sense amplifier and result in an RV-EVENT signal that is communicated to the digital controller/timer circuit 330. Similarly, ventricular depolarizations or R-waves in the LV-SENSE signal are sensed by a ventricular sense amplifier and result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

To simplify the description of FIGS. 4 through 6A–6B, it will be assumed that the following references to an "A-EVENT" and "A-PACE" will be the RA-EVENT and RA-PACE, respectively, if there is no LA pacing or sensing provided or programmably-enabled. Otherwise, these references will refer to the programmably-enabled one of the RA-EVENT or LA-EVENT and RA-PACE or LA-PACE, respectively.

The possible operating modes of IPG circuit 300 are depicted in the flow chart of FIG. 4 and described as follows. The particular operating mode of the present invention is a programmed or hard-wired sub-set of the possible operating modes as also described below. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace/sense electrode pair in step S118. The AV delay can be a PAV delay or SAV delay, depending upon whether it is started on an A-PACE or an A-EVENT, respectively, and is timed out by the SAV delay/PAV delay timer 372. The SAV delay or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV delay or PAV delay times out in step S102 without the detection of a non-refractory RV-EVENT or LV-EVENT. The TRIG_PACE window inhibits triggered pacing modes in response to a sense event occurring too early in the escape interval.

Either a programmed one or both of the RV-PACE and LV-PACE pulses are delivered in step S106 (as shown in the flow chart of FIG. 5) to selected RV and LV pace/sense electrode pairs, and the V-A escape interval timer is timed out in step S116. When both of the RV-PACE and LV-PACE pulses are delivered, the first is referred to as V-PACE1, the second is referred to as V-PACE2, and they are separated by a VP—VP delay. As described in greater detail below in reference to FIGS. 6A–6B, if a bi-ventricular pacing mode is programmed in step S106, it can be selectively programmed in a left-to-right ventricle (LV-RV) or right-to-left ventricle (RV-LV) pacing sequence wherein the first and second delivered ventricular pace pulses are separated by separately programmed VP—VP delays. The VP—VP delays are preferably programmable between about 4 msec and about 80 msec.

In accordance with the present invention, the QRS duration of a paced ventricular event following delivery of V-PACE2 to the selected RV or LV pace/sense electrode pair is selectively measured by a QRS duration timer 376 within the digital controller/timer circuit 330. The QRS duration timer 376 receives the output of an EGM sense amplifier in the EGM amplifiers circuit 390 that is coupled with a selected QRS duration sensing pair of pace/sense electrodes or with a pair of the housing sense electrodes 22, 24 and 26 to detect the far field EGM in a manner described in the above-referenced '966 patent. A slope and/or threshold detector can be employed in the EGM amplifiers circuit 390 for determining the start and end of the QRS waveform following V-PACE2. The pair of the housing sense electrodes 22, 24 and 26 that provide the highest amplitude or fidelity EGM signal is preferred because the far field more "global" EGM signal more closely approximates an ECG signal from external skin electrodes and the blanking time during and following delivery of the V-PACE2 pulse can be minimized.

Figure 6B:
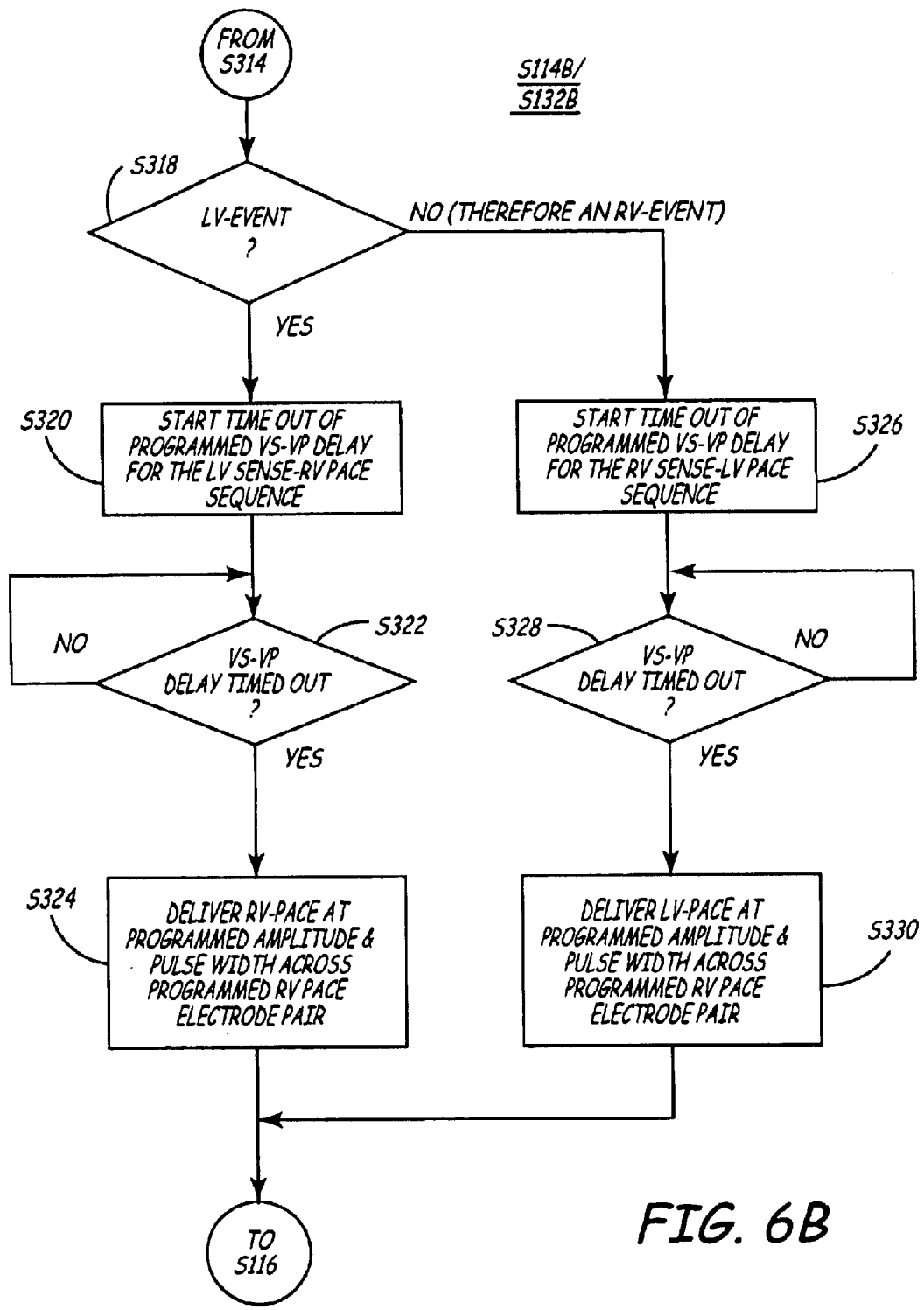

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular-triggered pacing mode is programmed to be operative during the AV delay. In accordance with the present invention, a ventricular-triggered pacing mode is programmed on, and it is undertaken and completed in step S114 (FIGS. 6A–6B). Any VSP mode that may otherwise be available is programmed off. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace/sense electrode pair in step S118, the AV delay is set to PAV delay in step S120, and the AV delay is commenced by AV delay timer 372.

If a non-refractory A-EVENT is sensed as determined in steps S122 and S134, then the V-A escape interval is terminated. The ABP and ARP are commenced by post-event timers 374 in step S134, the AV delay is set to the SAV delay in step S138, and the SAV delay is started in step S100 and timed out by SAV delay/PAV delay timer 372.

Assuming that the goal is to restore the normal activation sequence, a programmed SAV delay and PAV delay corresponding to a normal AV conduction time from the AV node to the bundle of His are used. Alternatively, SAV delay/PAV delay timer 372 may calculate the SAV and PAV delays in relation to the prevailing sensor rate or sensed intrinsic heart rate. The SAV delay may be timed from an RA-EVENT or LA-EVENT, and the PAV delay may be timed from an RA-PACE or an LA-PACE pulse.

At the expiration of the V-A escape interval in step S123, is it determined whether an RV-EVENT, LV-EVENT, or a collective V-EVENT (all hereinafter referred to as a "V-EVENT") is sensed across the RV tip sense electrode or the LV sense electrode. Next, it is determined whether this sensed event is a non-refractory V-EVENT in step S124. If the V-EVENT is determined to be a non-refractory V-EVENT, then the TRIG_PACE window is started or restarted, the V-A escape interval is restarted, and the post-ventricular time periods are restarted in step S126.

In step S128, it is determined whether a ventricular-triggered pacing mode is programmed to be operative during the V-A escape interval. Ventricular triggered pacing during the V-A escape interval is not programmed on, or is not provided in the pacing system, when triggered ventricular pacing is inappropriate for the patient. If ventricular triggered pacing during the V-A escape interval is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. Steps S130 and S132 are merely included herein to complete the disclosure of one form of an AV synchronous pacing system in which the present invention may be incorporated. It will be understood that the present invention can be incorporated into an AV synchronous pacing system that does not include steps S130 and S132.

Figure 5:
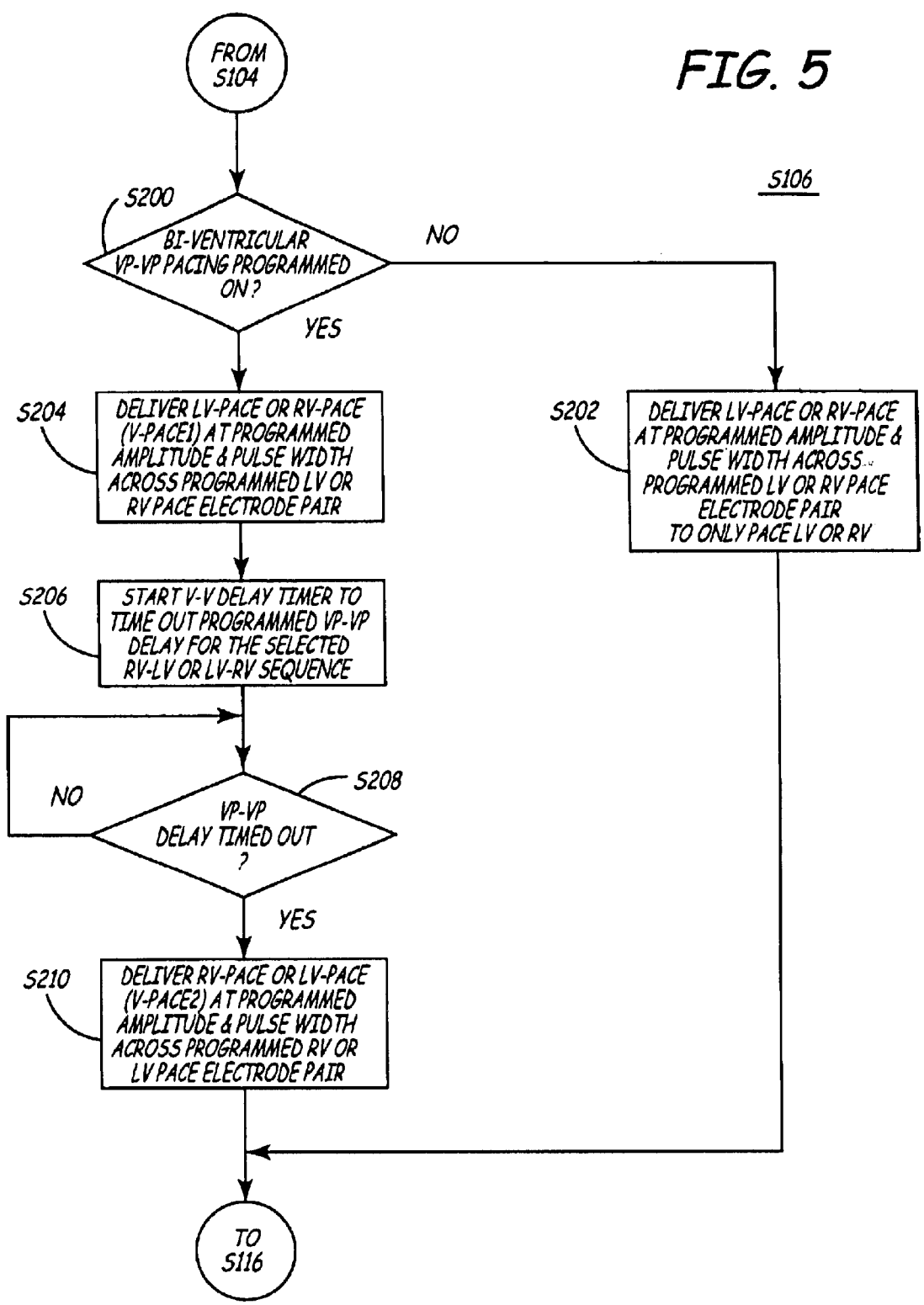
FIG. 5 is a flow chart illustrating the steps of delivering ventricular pace pulses following time-out of an AV delay in FIG. 4.

FIG. 5 depicts the step S106 in greater detail, and FIGS. 6A–6B depict the steps S114 and S132 in greater detail. If a VP—VP pacing mode is programmed on in step S106, it can be selectively programmed in a left-to-right or right-to-left ventricle sequence, wherein the first and second delivered ventricular pace pulses (V-PACE1 and V-PACE2) are separated by separately programmed VP—VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP—VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP—VP, VS/VP—VP, and VS-VP delays are preferably programmable between nearly 0 msec and about 80 msec.

As a practical matter, the minimum VS/VP—VP, and VP—VP delays may be set to one half the system clock cycle in order to avoid simultaneous delivery of RV-PACE and LV-PACE pulses. The pace pulse width is typically programmable between about 0.5 msec and 2.0 msec, and the pace pulse amplitude is typically programmable between 0.5 and 7.5 volts. The system clock provides a full clock cycle of about 8.0 msec. Therefore, the minimum VP—VP delay is set at a half clock cycle or about 4.0 msec.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP—VP delay timed out by V—V delay timer 366. If delivery of only a single RV-PACE or LV-PACE is programmed as determined in step S200, then it is delivered in step S202.

The present invention is operative when VS-VP, VS/VP—VP or VP—VP pacing modes are programmed on in order to measure the QRS duration of the ventricular depolarization occurring after delivery of V-PACE2 to obtain diagnostic trend data indicative of the state or progression of heart failure. In accordance with one aspect of the present invention, the optimal V—V delay, and optionally, the optimal PAV delay or SAV delay or the combination of such synchronous pacing delays that minimizes the measured QRS duration and maximizes mechanical heart performance is determined. All of the possible pacing modes are described herein before describing an implementation of these features of the invention.

If VP—VP pacing is programmed on in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected through the pace/sense electrode selection and control 350 depending on the desired RV pacing vector as set forth above, and also depending upon which electrodes are present in the system. And, the LV-PACE pulse is delivered across the active LV pace/sense electrode 50 and the IND_RV pace/sense electrode 38 in the trans-ventricular pacing path 60. The V-PACE1 pace pulse is delivered at a programmed pulse energy dictated by the programmed voltage and pulse width.

The V—V delay timer 366 is loaded with the programmed VP—VP delay and starts to time out in step S206. If the RV-PACE pulse is V-PACE1, then a programmed VP—VP delay is timed in V—V delay timer 366. The LV-PACE pulse can be delivered as V-PACE2 in the LV pacing path 60 between the active LV pace/sense electrode 50 and IND_RV pace/sense electrode 38 in step S210 after time-out of the programmed VP—VP delay in step S208. Conversely, if the LV-PACE pulse is the first to be delivered (V-PACE1) in the pacing path 60, then a programmed VP—VP delay is timed in V—V delay timer 366. The RV-PACE pulse is then delivered as V-PACE2 typically across the active RV pace/sense electrode 40 and the programmed indifferent electrode in step S210 after time-out of the programmed VP—VP delay in step S208.

Figure 4:
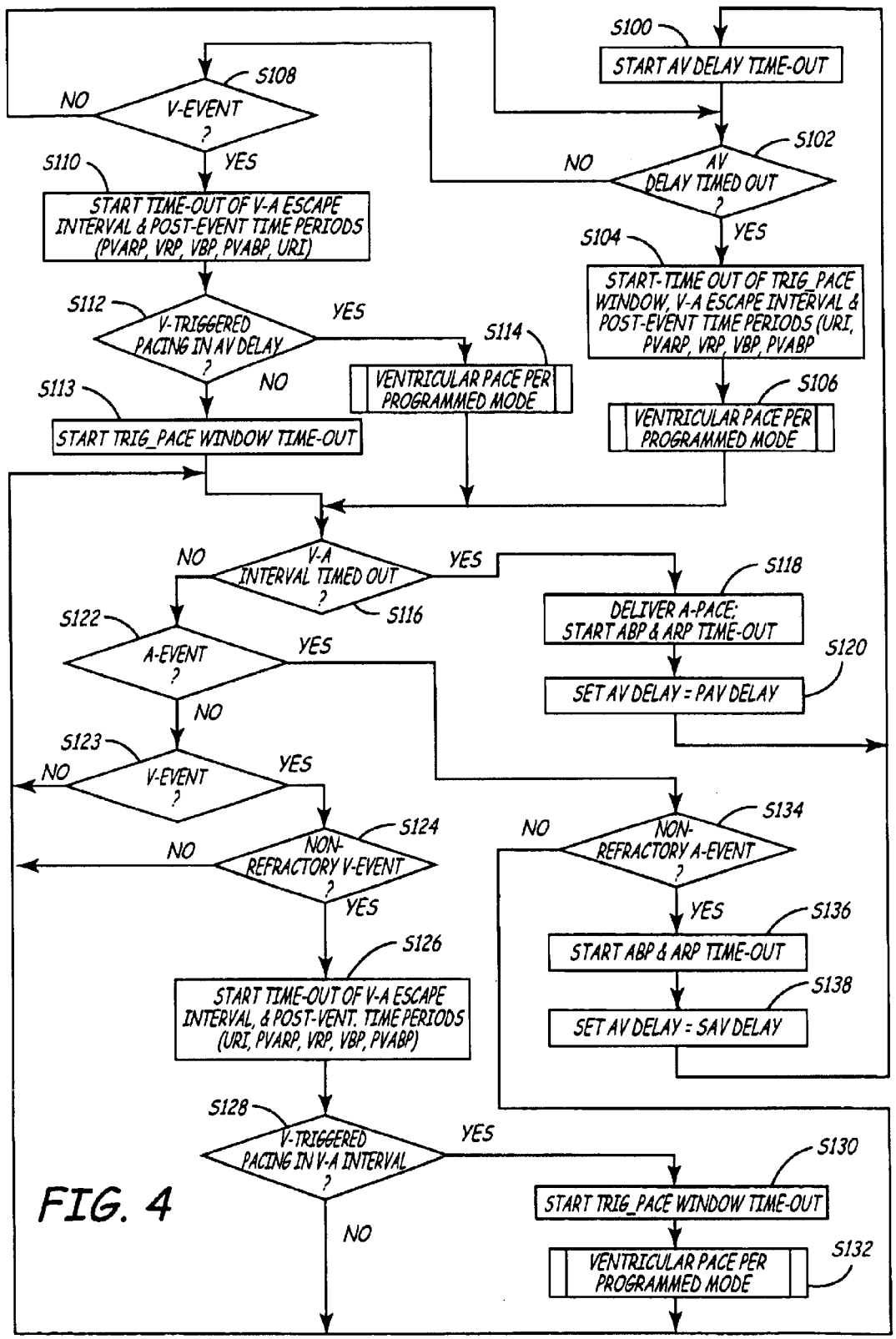
FIG. 4 is a comprehensive flow-chart illustrating the operating modes of the IPG circuitry of FIG. 3 in a variety of AV synchronous, bi-ventricular pacing modes in accordance with one embodiment of the invention.

FIG. 6A–6B is a flow chart illustrating the steps S114 and S132 of FIG. 4 for delivering ventricular pace pulses triggered by a ventricular sense event in step S108 during the time-out of an AV delay, or in step S124 during time-out of the V-A escape interval. It may be noted that these steps are optional, and may not be provided in Some devices, or alternatively, may be designed to be programmably enabled/disabled As noted above, the sensing of R-waves in the RV and LV can be accomplished by employing several RV-SENSE and LV-SENSE sensing axes or vectors and the trans-ventricular sensing vector. The selected vectors may include the bipolar RV-SENSE vector (RV sense electrodes 38 and 40), a unipolar RV-SENSE vector (RV tip sense electrode 40 and IND_CAN electrode 20), a unipolar LV-SENSE vector (LV sense electrode 50 and IND_CAN electrode 20), and a trans-ventricular, combined RV-SENSE and LV-SENSE vector (RV tip sense electrode 40 and LV sense electrode 50). The selection of the sensing vectors would depend upon heart condition and the selection of the pace pulse pathways.

The IPG circuit 300 can be separately programmed in one of three triggered pacing modes designated VS/VP, VS/VP—VP or VS-VP triggered modes for step S114. In the VS/VP triggered pacing mode, a V-PACE1 is delivered without delay upon a RV-EVENT or LV-EVENT to the RV or LV pacing pathway, respectively. In the VS/VP—VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP—VP delay times out. In the VS-VP pacing mode, a RV-EVENT or the LV-EVENT starts time-out of a VS-VP delay, and a single pace pulse (designated V-PACE2) is delivered to the selected LV or the RV pace/sense electrode pair, respectively, when the VS-VP delay times out.

The TRIG_PACE time window started by a prior V-EVENT or V-PACE must have timed out in step S300 prior to delivery of any triggered ventricular pace pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP—VP triggered mode as determined in step S304, the non-refractory RV-EVENT or LV-EVENT or collective V-EVENT of indeterminable origin is treated as a single V-EVENT. If the TRIG_PACE window has timed out as determined in step S300, then the single V-EVENT triggers the immediate delivery of a programmed one of the RV-PACE or a LV-PACE as V-PACE1 across the programmed bipolar or unipolar RV and LV pace/sense electrode pair, respectively, in step S306. Thus, V-PACE1 is delivered to a predetermined RV or LV pace/sense electrode pair, regardless of whether a RV-EVENT and LV-EVENT is sensed.

Then, a VS/VP—VP delay is started in step S308 and timed out in step S310. The VS/VP—VP delay is specified as a VP—VP delay when the RV-PACE is V-PACE1 and the LV-PACE is V-PACE2. The VS/VP—VP delay is specified as a VP—VP delay when the LV-PACE is V-PACE1 and the RV-PACE is V-PACE2. The LV-PACE or RV-PACE pulse is delivered at the programmed amplitude and pulse width across the programmed LV or RV pace/sense electrode pair in step S210.

In the simplest embodiment of the present invention, the VS/VP—VP mode would be the only triggered ventricular pacing mode provided. The remaining steps of FIGS. 6A and 6B are described in the event that the VS/VP and/or the VS-VP triggered ventricular pacing mode is included in the pacing system.

In step S314, it is determined whether the VS-VP triggered pacing mode or the VS/VP triggered pacing mode is programmed. When the IPG circuit 300 is programmed to a single heart chamber VS/VP triggered pacing mode, the RV-EVENT or LV-EVENT triggers the immediate delivery of an RV-PACE or an LV-PACE across a programmed bipolar or unipolar RV or LV pace/sense electrode pair, respectively, in step S316, regardless of whether an RV-EVENT or LV-EVENT was sensed.

When the IPG circuit 300 is programmed to the VS-VP triggered pacing mode, an LV-EVENT as determined in step S318 loads the appropriate VS-VP delay in V—V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay is loaded in V—V delay timer 366 in step S326, and the VS-VP delay is timed out in step S328. The LV-PACE (also designated V-PACE2) is delivered at time-out of the VS-VP delay in step S330.

Returning to FIG. 4, the V-A escape interval is timed out in step S116 following the completion of the ventricular pacing mode of FIGS. 6A–6B. If the V-A escape interval times out, then an RA-PACE pulse is typically first delivered across the RA pace/sense electrodes 17 and 19 in step S118, and the AV delay timer is restarted in step S100.

Thus, it will be observed that the multi-site, AV sequential, bi-ventricular cardiac pacing system described above is selectively programmable to provide ventricular pacing pulses delivered to one or both of the RV and LV sites synchronously within a V—V delay following time-out of an AV delay from a preceding delivered A-PACE pulse or an A-EVENT (typically, the RA-PACE pulse or the RA-EVENT) and operating in accordance with the steps of: (a) timing an AV delay from a preceding delivered A-PACE pulse or A-EVENT; (b) detecting a V-SENSE at one of a first and second ventricular site within the AV delay and, in response, terminating the AV delay and providing a V-EVENT; (c) delivering a V-PACE1 pulse to a selected one of the first and second ventricular sites upon the time-out of the AV delay or, in a triggered mode, upon the V-SENSE; (d) timing a V—V delay comprising one of a VS-VP pace delay from a V-EVENT that occurred prior to the time-out of the AV delay, or alternatively, timing a VP—VP pace delay from the V-PACE1 delivered at the end of the AV delay, or timing a VS/VP—VP pace delay from a triggered V-PACE1; and (e) delivering a V-PACE2 pulse to the other of the first and second ventricular sites upon the time-out of the V—V delay.

FIG. 7 illustrates the overall IMD function starting from the time of implantation (step S400), initial programming (steps 402), and baseline parameter measurements (step S404). The illustrated steps continue through successive cycles of gathering parameter data in the IMD (steps S406–S418), and uplink telemetry transmission of the accumulated data to an external programmer (steps S422–S424) for display and analysis (step S426). This may result in possible reprogramming (step S402) and baseline parameter measurement (step S404) to better assess the heart failure state. Optionally, the pacing parameters, particularly the SAV delay, PAV delay and/or the V—V delay, can be adjusted and the optimal QRS duration determined again in step S420 illustrated in greater detail in FIG. 8. The present invention may be implemented into a versatile multi-chamber pacing system as described above, or into a less comprehensive pacing system offering fewer programmable pacing parameters and operating modes.

Each pacing parameter may be programmably enabled. A particular event trigger for initiating the measurement of the programmably enabled parameter, as well as any specific measurement criteria, can be programmed in step S402. This may be accomplished using conventional downlink telemetry transmitted commands that are received in the telemetry transceiver 332 and forwarded to the digital controller/timer circuit 330. The physician may initially program the pacemaker to deliver a bi-ventricular stimulation therapy in accordance with selected options provided in the flow charts of FIGS. 4, 5 and 6A–6B as described above.

In step S404, baseline parameter measurements are optionally performed for each programmably-enabled parameter to collect baseline or reference parameter data. In particular, the QRS duration reference or $QRS\_DUR_{REF}$ data may be collected. This data may be stored in RAM 310 and transmitted to the external programmer for observation by the physician. It may further be used to program the operating modes and parameter values, e.g., the LRL SAV, PAV, and/or V—V delays. The determined $QRS\_DUR_{REF}$ value represents the optimal, shortest, QRS duration that can be obtained by adjustment of the SAV delay, PAV delay and/or V—V delay in steps S402 and S404. The SAV delay, PAV delay and/or V—V delay are programmed to the SAV delay, PAV delay and/or V—V delay determined in step S404. The initial $QRS\_DUR_{REF}$ value is then stored in the IMD memory and also stored externally in a patient file maintained by the physician with a date and time stamp and other pertinent data such as patient activity level measured by activity signal processor circuit 332 and patient heart rate and stability.

Periodically, the programmably-enabled parameters including the $QRS\_DUR_{SAMPLE}$ values are measured in step S418 and stored in step S420. This may be performed when an event trigger parameter occurs. In addition, an algorithm to adjust the V—V, SAV, and/or PAV delays to provide a measured QRS_DUR$_{MIN}$ value can be entered and performed in step S422 as shown in detail in FIG. 8. The event criteria of step S406 may be a programmed time or multiple times of every day. Alternatively, specified days of the week or month, or the detection of a patient-initiated parameter measurement may be utilized as the trigger. Other programmed event such as a combination of one or more times of day, and/or a level of patient exercise indicated by the activity signal processor circuit 332 may also provide the trigger condition.

Preferably, the measurement of the QRS duration to derive QRS_DUR$_{SAMPLE}$ data or to develop a derive QRS_DUR$_{MIN}$ pursuant to step S422 should take place when the heart rate is in a normal range and is stable within a certain stability tolerance. This criteria can be programmed by the physician and are determined over a series of heart cycles in steps S408 S412 in a manner well known in the art. In one embodiment of the invention, the measurement of the QRS duration is only performed in step S418 when the patient is at rest or within a programmed exercise range as determined in step S414. Typically, in step S408, incidences of spontaneous RA-EVENTs and RV-EVENTs would be monitored while the escape interval establishing the pacing rate is set to the LRI to determine the intrinsic heart rate. The heart rate would be established by the pacing lower rate if the rate cannot be determined in this way.

In this particular case, the determination of a single QRS_DUR$_{SAMPLE}$ data point in step S418 would be conducted within one heart cycle. In this instance, heart rate, heart stability and activity level changes would not be measured when that single data point is derived. Alternatively, heart rate, stability and activity level changes become more pertinent if the IMD is programmed to derive an average QRS_DUR$_{SAMPLES}$ maximum, and/or minimum QRS_DUR$_{SAMPLE}$ values over a programmed number of heart cycles and sample values. Therefore, FIG. 7 depicts the possible operation wherein the heart rate, heart stability, and patient activity level are re-determined in steps S408 through S414 before each QRS duration measurement or the programmed series is undertaken. The determination of average QRS_DUR$_{SAMPLE}$, maximum, and minimum QRS_DUR$_{SAMPLE}$ values in step S418 may be aborted if the heart rate, stability and/or activity level changes such that the criteria is no longer satisfied before the parameter measurement steps are completed.

According to another aspect of the invention, the algorithm may determine one or more of the settings of the SAV delay, PAV delay and/or V—V delay parameters that achieve the shortest QRS_DUR$_{MIN}$ value. This is shown in step S422. In this embodiment, a programmable delay of a number of heart cycles is provided between each adjustment of a parameter value and the measurement of the QRS_DUR$_{SAMPLE}$ value to allow the heart to stabilize as described further below. The shortest achievable QRS_DUR$_{SAMPLE}$ value is retained in memory as the QRS_DUR$_{MIN}$ value along with the particular settings of the V—V, SAV, and/or PAV delay that provides that QRS_DUR$_{MIN}$ value. These parameter settings are then employed in the operation of the pacing system pursuant to FIGS. 4 through 6B until they are derived again. As in the embodiment described in the foregoing paragraph, the calculation of these parameters may be aborted if the heart rate, stability and/or activity level changes such that predetermined criteria is no longer satisfied before the calculations are completed.

The QRS duration is measured as described above following the delivery of a V-PACE2 to the RV or LV after a V-PACE1 or a V-EVENT occurs in the other of the LV or RV after time-out of the governing one of the VS-VP, VSNVP-VP or VP—VP delays. Then, the single or average, QRS_DUR$_{SAMPLE}$ value and maximum and minimum QRS_DUR$_{SAMPLE}$ values are obtained. As noted above, the QRS duration measurement preferably takes place using a selected pair of the housing sense electrodes 22, 24, 26 coupled to the EGM sense amplifiers circuit 390, although other electrode pairs can be selected via pace/sense selection and control 350.

The completed one or more of a single or average, maximum, and minimum QRS_DUR$_{SAMPLE}$ values is stored in IMD memory with a date, time stamp and any other pertinent information such as heart rate and patient activity level, in step S420. Steps S406 through S418 are repeated each time that the event trigger criteria for the QRS duration measurement are satisfied. The data collection continues over many days or months until the initiation of a telemetry session by the physician and uplink telemetry transmission of the accumulated parameter data in steps S424 and S426. The history of the number, times and dates of successive parameter measurements can also be stored in IMD memory, but the stored parameter data and related data may be discarded on a FIFO basis if the memory capacity assigned to such data storage is exceeded. The physician then reviews the accumulated data in step S428 and can reprogram the values of the AV delays and the V—V delay, which can either be RV-LV delay and/or the LV-RV delay, repeating steps S402 and S404.

In S422, changes are automatically made to the SAV delay, PAV delay and/or V—V delay to derive a minimum QRS duration (QRS_DUR$_{MIN}$) from a series of measured QRS$_{13}$ DUR$_{SAMPLE}$ values obtained by dithering the values of one or more of the V—V delay, the SAV delay and the PAV delay. Step S422 can be programmed on or off and thereby bypassed in FIG. 7. No parameter changes are made if step S422 is disabled, but the physician still obtains valuable data illustrating the trend in QRS duration in the course of following the steps of FIG. 7 that can be analyzed to determine whether the patient's heart failure state is improving or deteriorating. If it appears that the QRS duration is remaining stable or shortening over time, then it may be presumed that the applied pacing therapy and drug therapy is of benefit. If the QRS duration is lengthening, then adjustments in therapy, including repeating steps S402 and S404 to determine if it can be shortened, need to be undertaken.

In one variation of this aspect of the invention, the SAV, PAV and/or V—V delays providing the minimum QRS duration is derived by successively applying incremented or decremented ones of the SAV delay, PAV delay and/or V—V delay, deriving a QRS$_{13}$ DUR$_{SAMPLE}$ value at each adjusted delay, comparing the set of N derived QRS_DUR$_{SAMPLE}$ values to determine the minimum QRS$_{13}$ DUR$_{SAMPLE}$ value, and setting the SAV delay, PAV delay and/or V—V delay to the SAV delay, PAV delay and/or V—V delay that provides the minimum QRS_DUR$_{SAMPLE}$ value.

Figure 8:
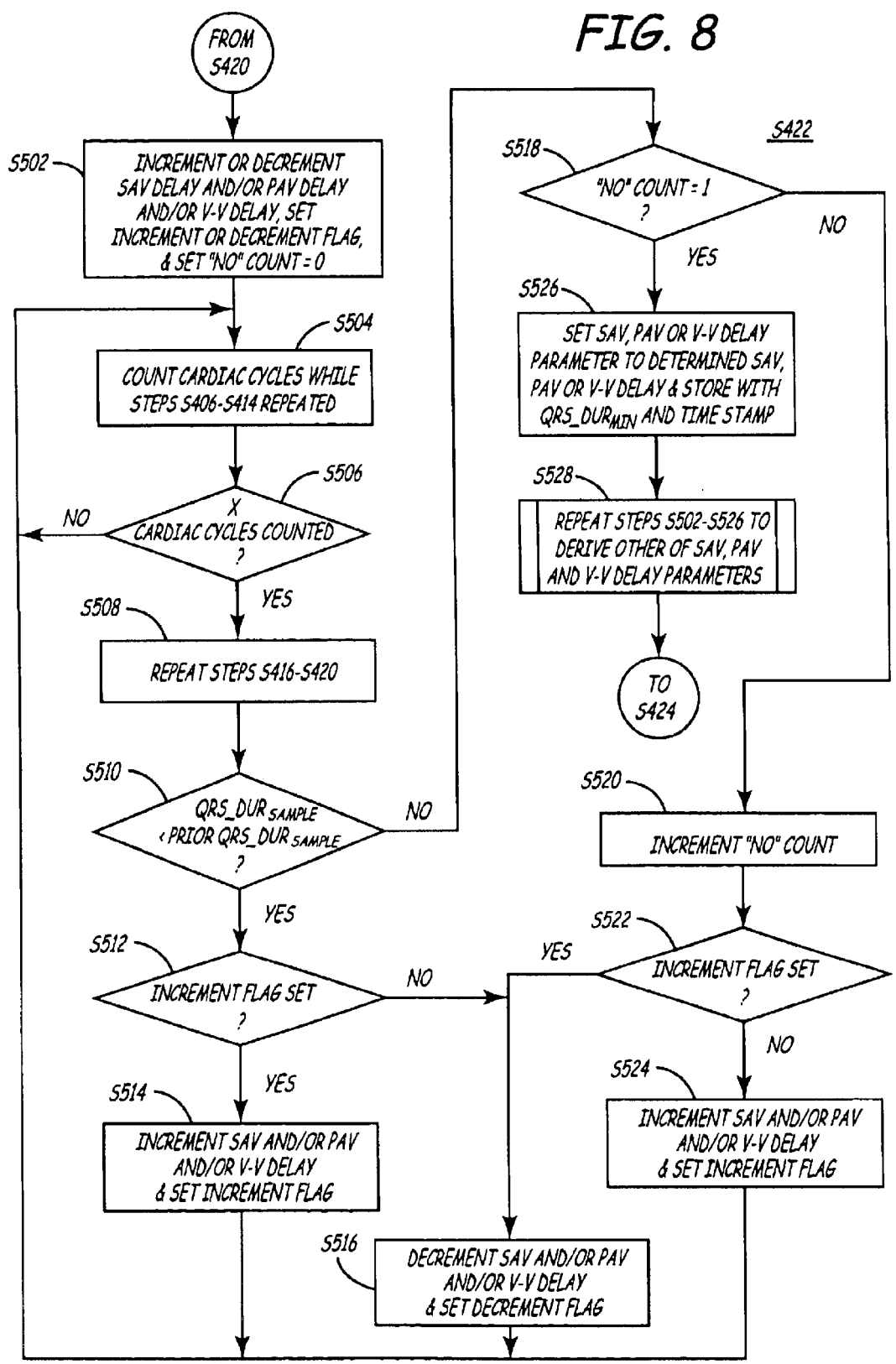
FIG. 8 is a flow chart illustrating the steps of adjusting synchronous pacing delays including one or more of the V—V delay, the SAV delay and the PAV delay as a function of changes in QRS duration.

One manner of determining the values of the SAV delay, PAV delay, and/or V—V delay that provide a minimal QRS duration (QRS DURMIN) following delivery of the V-PACE2 is Illustrated in FIG. 8. At this point, the first measured QRS_DUR$_{SAMPLE}$ value at the prevailing V—V delay, SAV delay and PAV delay has been stored in step S420. Each of a series of QRS_DUR$_{SAMPLE}$ values that are measured after a change in one or more of the V—V delay, SAV delay, and PAV delay are compared with the preceding or prior measured $QRS\_DUR_{SAMPLE}$ value to determine if the change has decreased the QRS duration. An additional change in the same direction (increasing or decreasing the parameter duration) is made if the prior change does decrease the QRS duration. If, however, the change results in an increase in the measured QRS duration, then the change direction is reversed to repeat the measurement of the QRS duration using the prior parameter value. Only one reversal in direction is allowed to inhibit "hunting" that could otherwise occur and cause the algorithm to repeat the dithering indefinitely. A rest period of a number of heart cycles or a time period is provided between each change in a V—V delay, SAV delay, and PAV delay parameter value to allow the heart to acclimate to the change.

Thus, in step S502 one or more of the SAV, PAV, and/or V—V delays are either incremented or decremented, the corresponding increment or decrement flag is set so that the direction of change (increase or decrease) is recorded, and a "NO" count is set to "0". Next, the resting period is timed or counted in steps S504 and S506. It will be understood that a physician may establish an incrementing and decrementing routine from the patient work-up in steps S402 and S404 to determine which of the parameters and combinations of parameters effect a change in the QRS duration in the particular patient. The physician may also program increment and decrement amounts and the length of the resting period of steps S504 and S506. In another embodiment, the physician may also program the system to abort or continue the process after a delay if steps S410 or S414 are not satisfied.

At this point, steps S416–S420 are repeated per step S508 to derive a succeeding measured $QRS_{13}\ DUR_{SAMPLE}$ value at the decremented or incremented one or more of the V—V, SAV, and/or PAV delays that is can be stored in memory in step S420 to retain a record of the operation of the algorithm for retrieval and review by the physician in a subsequently initiated telemetry session. The succeeding measured $QRS_{13}\ DUR_{SAMPLE}$ value is compared to the prior measured $QRS\_DUR_{SAMPLE}$ value in step S510. If the succeeding measured $QRS\_DUR_{SAMPLE}$ value is less than the prior measured $QRS\_DUR_{SAMPLE}$ value, then the flag status is checked in step S514. If the increment flag was set in step S502, and the increment has effected the favorable reduction in the QRS duration, then the one or more of the SAV delay and/or PAV delay and/or V—V delay that was incremented in step S502 is again incremented in step S514. Similarly, if the decrement flag was set in step S502, and the decrement has effected the favorable reduction in the QRS duration, then the one or more of the SAV, PAV, and/or V—V delay that was decremented in step S502 is again decremented in step S516. The process of steps S504–S516 is then repeated to determine if the QRS duration can be further reduced.

Returning to step S510, if the succeeding measured $QRS_{13}\ DUR_{SAMPLE}$ value is greater than the prior measured $QRS\_DUR_{SAMPLE}$ value, which can occur in the first pass through steps S502 through S508 or in subsequent passes through S504–S516, then a change in direction is initiated. The "NO" count (set to "0" in step S502) is tested in step S518 and incremented to "1" in step S520. The flag status is tested in step S522 to determine the prevailing direction of change, and the change in direction is effected in step S516 or S524. Thus, if the one or more of the SAV, PAV, and/or V—V delays was decremented previously, then the direction is changed in step S524 to increment the one or more of the SAV delay and/or PAV delay and/or V—V delay and to repeat steps S504–S510.

At some point, the succeeding measured $QRS\_DUR_{SAMPLE}$ value is greater than the prior measured $QRS\_DUR_{SAMPLE}$ value, and the condition of step S518 is satisfied. Then, the prior measured $QRS_{13}\ DUR_{SAMPLE}$ value is declared the $QRS\_DUR_{MIN}$ value, and it and the corresponding one or more of the SAV, PAV, and/or V—V delays are stored in RAM and employed in the operating system as described above with respect to FIGS. 4 through 6B until step S422 is repeated upon a trigger event satisfying step S406.

Alternatively, the incremented or decremented preceding value of the one or more of the SAV delay and/or PAV delay and/or V—V delay are stored in RAM and employed in the operating system as described above with respect to FIGS. 4 through 6B until step S422 is repeated upon a trigger event satisfying step S406 the first time the condition of step S510 is not satisfied.

The physician can also enter programming commands that enable successive changes in each of the SAV delay, PAV delay and V—V delay to be tested pursuant to steps S502 S526 and the above-described variants. Therefore, the next one of the synchronous pacing delays can be tested after a previous synchronous pacing delay has been derived by repeating steps S502–S526 pursuant to step S28 until all of the delay values have been derived. In many clinical cases, only the optimal V—V delay in the RV-LV or LV-RV sequence would be obtained. In other clinical cases, the optimal SAV delay would be first obtained, and then the optimal V—V delay in the RV-LV or LV-RV sequence would be obtained. In certain clinical cases, the PAV delay would be automatically set to substantially the same value as the optimal SAV delay derived through executing any of the various combinations of steps S502–S526. The order of the process and the tests included in the process can be left to the clinicians to develop for the particular patient.

The resulting values of the SAV delay, PAV delay and/or the V—V delay may be stored with the corresponding $QRS\_DUR_{SAMPLE}$ data and the other related data in step S526. This data may be employed in the operating system depicted in FIGS. 4 through 6B until the event criteria are next satisfied. Therefore, in this aspect, the present invention can be employed to selectively derive the SAV, PAV, and/or the V—V delays that optimally minimizes the QRS duration over a period of weeks or months until the physician is able to analyze the stored data in step S428, and optionally perform steps S402 and S404 if deemed desirable.

The preceding specific embodiments are illustrative of the practice of the invention. It is to be understood, therefore, that other expedients known to those of skill in the art or disclosed herein may be employed.

The preceding specific embodiments are directed to RV and LV pacing in a programmed RV-LV or LV-RV sequence. Such pacing is in response to the occurrence of a V-EVENT sensed in, or a V-PACE1 delivered to, the RV or LV. However, it will be understood that the present invention also embraces locating first and second ventricular pace/sense electrodes in either the RV or LV separated apart from one another. In this case, the V-PACE1 and/or V-PACE2 are delivered in one of the VS/VP, VS/VP—VP, or VS-VP triggered pacing modes to the first and/or second ventricular pace/sense electrodes to provide for triggered pacing on a V-EVENT detected during the AV delay only.

All patents and publications referenced herein are hereby incorporated by reference in there entireties.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of an AV synchronous, three or four chamber pacemaker that are not disclosed and are not necessary to the practice of the present invention. In addition, it will be understood that specifically described structures, functions and operations set forth in the above-incorporated patents and publications can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A cardiac pacing system for delivering electrical stimulation to at least three chambers of a heart, said at least three chambers including a left ventricular chamber and a right ventricular chamber wherein the left ventricular chamber and the right ventricular chamber do not synchronously contract, comprising:

a timing circuit to measure at least one time interval, the at least one time interval operatively coupled to control delivery of an electrical stimulatIon therapy to at least one of a left ventricular chamber and a right ventricular chamber by a cardiac pacing system;

a sensing circuit to measure a duration of a ORS complex of only a last-to-depolarize ventricular chamber of the heart; and a control circuit coupled to the timing circuit and the sensing circuit to adjust the length of the at least one time interval based on the measured duration of the QRS complex of the last-to-depolarize ventricular chamber of the heart.

2. A system according to claim 1, wherein the sensing circuit includes a circuit to sense a depolarization in a selected one of the left or right atria of the heart, and wherein the at least one time interval further comprises an sensed A-V (SAV) delay initiated upon sensing of the depolarization, and further comprising:

an output circuit coupled to the timing circuit to:

a) deliver a first ventricular pacing pulse to a first ventricular site disposed in a first ventricular chamber upon expiration of the SAV delay and a second ventricular placing pulse to a second ventricular site disposed in a second ventricular chamber, wherein said second ventricular pacing pulse is delivered after a temporal interval following delivery of said first ventricular pacing pulse, or b) upon detecting a ventricular depolarization in said first ventricular chamber prior to expiration of the SAV delays withholding delivery of the first ventricular pacing pulse and delivering the second ventricular pacing pulse after a temporal interval following detection of said ventricular depolarization, or c) upon detecting a ventricular depolarization in said second ventricular chamber prior to expiration of the SAV delay, withholding delivery of the second ventricular acing pulse and delivering the first ventricular pacing pulse after a temporal interval following detection of said ventricular depolarization.

3. A system according to claim 2, wherein the output circuit includes a circuit to deliver an atrial pacing pulse to the selected one of the left or right atria of the heart upon expiration of a V-A escape interval, and wherein the at least one time interval includes a paced A-V (PAV) delay initiated upon delivery of the atrial pacing pulse, and wherein the output circuit further comprises a circuit to deliver the first ventricular pacing pulse to the first ventricular site upon expiration of the PAV delay.

4. A system according to claim 2, wherein the temporal interval comprises a bi-ventricular delay.

5. A system according to claim 4, wherein the first ventricular chamber is a location within the right ventricle of the heart and the second ventricular chamber is a location within the left ventricle of the heart.

6. A system according to claim 4, wherein the first ventricular chamber is a location within the left ventricle of the heart and the second ventricular chamber is a location within the right ventricle of the heart.

7. A system according to claim 4, wherein the output circuit includes a circuit to deliver a pacing pulse to the other one of the left or right atria of the heart.

* * * * *